(12) United States Patent
Thiel et al.

(10) Patent No.: US 8,129,126 B2
(45) Date of Patent: Mar. 6, 2012

(54) USE OF THE 4-1BB RECEPTOR FOR IDENTIFYING AND/OR SEPARATING ACTIVATED REGULATORY TH CELLS (TREG)

(75) Inventors: Andreas Thiel, Berlin (DE); Anne Schönbrunn, Berlin (DE); Marco Frentsch, Berlin (DE)

(73) Assignee: Miltenyi Biotec GmbH, Bergisch Gladbach (DE)

( * ) Notice: Subject to any disclaimer, the term of this patent is extended or adjusted under 35 U.S.C. 154(b) by 192 days.

(21) Appl. No.: 12/294,181

(22) PCT Filed: Mar. 26, 2007

(86) PCT No.: PCT/EP2007/002860
§ 371 (c)(1),
(2), (4) Date: Mar. 17, 2009

(87) PCT Pub. No.: WO2007/110249
PCT Pub. Date: Oct. 4, 2007

(65) Prior Publication Data
US 2010/0055720 A1    Mar. 4, 2010

(30) Foreign Application Priority Data

Mar. 24, 2006  (DE) .......................... 10 2006 014 193
Mar. 28, 2006  (EP) ..................................... 06090038

(51) Int. Cl.
*G01N 33/53*    (2006.01)
(52) U.S. Cl. ....................................................... 435/7.1
(58) Field of Classification Search ........................ None
See application file for complete search history.

(56) References Cited

U.S. PATENT DOCUMENTS

| 2003/0049696 | A1 | 3/2003 | Norment et al. | |
| 2005/0095244 | A1 * | 5/2005 | Jure-Kunkel et al. | 424/144.1 |
| 2007/0172947 | A1 * | 7/2007 | Shirwan | 435/325 |
| 2007/0292431 | A1 * | 12/2007 | Zheng et al. | 424/142.1 |

FOREIGN PATENT DOCUMENTS

| EP | 1 530 972 A2 | 5/2005 |
| WO | 2004/104185 A1 | 12/2004 |
| WO | 2005/124346 A1 | 12/2005 |

OTHER PUBLICATIONS

Wolfl et al., Cytometry Part A, 2008, 73A: 1043-1049.*
BD Pharmingen TM: "Technical Data Sheet: PE conjugated mouse anti-human CD137 (4-IBB)" [Online], May 7, 2005, p. 1, Retrieved from the Internet: URL:http://www.bdbi osci ences. com/external_fi l es/pm/doc/tds/human/1i ve/web_enabled/36 005X_555956.pdf>, retrieved on: Aug. 18, 2006.
Hori S. et al.: "Control of regulatory T cell development by the transcription factor Foxp3" in Science, American Association for the Advancement of Science, US, vol. 299, No. 5609, Feb. 14, 2003, pp. 1057-1061.
Zheng Guoxing et al.: "Induction of antitumor immunity via intratumoral tetra-costimulator protein transfer" in Cancer Research, American Association for Cancer Research, Baltimore, MD, US, vol. 61, No. 22, Nov. 15, 2001, pp. 8127-8134.
Pauly, Susanne et al.: "CD137 is expressed by follicular dendritic cells and costimulates B lymphocyte activation in germinal centers" in Journal of Leukocyte Biology, vol. 72, Jul. 2002, pp. 35-42.
Wikipedia : "Regulatorische T-Zelle", [Online], Retrieved from the Internet: URL:http://de.wikipedia.org/wiki/Regulatorische_T-Zelle, [retrieved on Oct. 23, 2009].
Groux, "An overview of regulatory T cells," in Microbes and Infection, vol. 3, 2001, pp. 883-889.

* cited by examiner

*Primary Examiner* — Ilia Ouspenski
(74) *Attorney, Agent, or Firm* — Joyce von Natzmer; Pequignot + Myers LLC (57) ABSTRACT

The invention relates to the use of the 4-1BB receptor for identifying and/or separating specific regulatory Th cells after activation with an antigen, polyclonal regulatory Th cells after polyclonal activation and to a method for the identification and/or separation of regulatory Th cells, the regulatory T cells being detected on the basis of the expression of the 4-1BB receptor by an antibody, an antigen or ligands which are coupled to a fluorescent substance, haptenes or magnetic microparticles. The invention also relates to a kit comprising an antibody, an antigen or ligands for detecting the 4-1BB receptor for the identification and/or separation of a regulatory Th cell, the antibody being coupled to a fluorescent substance, haptenes or magnetic microparticles.

15 Claims, 8 Drawing Sheets

USE OF THE 4-1BB RECEPTOR FOR IDENTIFYING AND/OR SEPARATING ACTIVATED REGULATORY TH CELLS (TREG)

This is the U.S. national stage of International application PCT/EP2007/002860, filed Mar. 26, 2007 designating the U.S. and claiming priority to German application DE 10 2006 014 193.8, filed Mar. 24, 2006 and European application EP 06090038.8 filed Mar. 28, 2006.

The present invention relates to the use of a 4-1BB receptor for identifying and/or separating activated regulatory T cells and to a kit comprising an antibody for detecting the 4-1BB receptor (CD137) for identifying and/or separating activated regulatory Th cells, where the antibody is coupled to a fluorescent substance or magnetic microparticle. The regulatory T cells may in this connection be activated both polyclonally and with specific antigens. The activation can take place in vitro or even in vivo.

Specific T cells which actively suppress unwanted immune responses such as, for example, to endogenous structures (autoantigens) exist in the organism. They are referred to as regulatory T cells (Treg). Regulatory T cells are essentially involved in the life-long maintenance of peripheral tolerance to autoantigens. They are produced in the thymus, but the activity thereof is greatly reduced with increasing age.

Regulatory T cells may lead to suppression of anti-tumor responses (Onizuka et al., Cancer Res. 59: 3128-3133 (1999); Shimizu et al., J. Immunol. 163:5211-5218 (1999)) because many tumor antigens represent classical autoantigens. By contrast, reduced numbers of Treg or functional alterations in Treg may lead to autoimmune diseases during which endogenous structures are attacked in an uncontrolled manner like foreign substances or pathogens.

Tregs are involved in maintenance of immunological self-tolerance since they inhibit the activation of autoreactive T cells. They are capable of suppressing both cytokine production and proliferation of such potentially pathogenic T cells. An essential step in identifying regulatory T-helper cells was the characterization of CD4+ T-helper cells which include the alpha chain of the interleukin-2 (IL-2) receptor (CD25) constitutively as surface membrane protein. The functional significance and the exact molecular mechanisms of the suppression of these CD25+ CD4+ regulatory T cells and how they arise have not been elucidated. Since the CD25 receptor is also expressed by subpopulations of non-regulatory T cells, this marker can be used only provisionally for analyzing and concentrating Treg. In particular, however, CD25 cannot be used for identifying and separating activated antigen-specific regulatory T cells.

Isolation of Treg and in particular of Treg specific for particular antigens is, nevertheless, one of the great therapeutic aims. Likewise the analysis of antigen-specific Treg! (Auto)antigen-specific Tregs are a specific means for suppressing unwanted immune responses such as, for example, autoimmune reactions in rheumatoid arthritis (RA), multiple sclerosis (MS), atherosclerosis (AS), diabetes, psoriasis. Other unwanted immune responses in which Treg would represent a specific means are GvHD (graft versus host disease) in allogeneic stem cell transplantations or transplant rejection in organ transplantations (Hara et al., J. Immunol. 166:3789-3796(2001); Taylor et al., J. Exp. Med. 193:1311-1318 (2001). Allergies also represent unwanted immune responses for which only a few therapeutic options have been available to date. A therapeutic treatment with Treg which is based on the natural principle of peripheral tolerance and has been demonstrated in many experimental models would include no side effects by comparison with conventional immunosuppressive medicaments and would be curative.

In relation to the stated importance of Tregs, the molecules and mechanisms involved in the suppression, and reliable Treg markers, are of great importance. A molecular biological Treg marker, the transcription repressor FoxP3 which belongs to the Forkhead family, is acknowledged in the art (Hori et al (2003) Science 99(5609):1057-61). In addition, regulatory T cells can be identified on the basis of expression of the CD25 molecule (Thornton and Shevach (1998) J. Exp. Med. 188 287-296; Sakaguchi et al (1995) J. Immunol. 155 1151-1164).

Choi et al 2004, JLB, disclose that no evidence yet exists that 4-1BB can be employed as discriminatory marker for Treg versus CD25 negative cells.

However, it has not been possible in particular to identify and isolate Treg which recognize a specific antigen. This would be possible if specifically activated Treg could be separated and would be a basic prerequisite for specific therapies with Treg for example for autoimmune diseases, in which the autoimmune reactivities underlying the disease should be suppressed, but not immunoreactivities in relation to tumor cells.

It is thus difficult in the present state of the art to identify and/or isolate regulatory T cells. Markers described above do not allow the possibility of identifying the totality of regulatory T cells because not all regulatory T cells express definedly specific markers.

Accordingly, it has been possible to identify and/or separate only subpopulations, such as, for example, only the Treg which strongly express the CD25 receptor. It is further possible for various other cell subpopulations to have the same cell surface markers (such as CD4 for Th1 Th2, or other Th cells or CD25 for activated T cells or B cells.

However, it is not possible in particular to identify activated Treg after stimulation with defined antigens by means of specific activation markers. Although activation of regulatory Th cells leads to enhanced expression of CD25 and CD38, they are expressed like all other described T-cell activation markers also in other T cells, so that it has not been possible to separate any antigen-specific Treg by means of specific activation markers.

Most of the methods which identify and/or isolate regulatory Th cells on the basis of the expression of a particular cell surface marker depend on recognition of a marker and binding of an antibody. If it is not possible to use a single marker in order to identify and/or isolate a particular cell type, it is necessary to find a combination of markers and the antibodies appropriate for them (Levingset al., J Exp. Med. 193(11): 1295-1302 (2001)). Such experiments may in practice be very complicated and difficult to carry out. It is moreover possible for binding of the antibodies to influence the activity of the target cell or expression of the other markers, thus having a negative influence on the identification and/or separation process with the other antibodies.

It should also be mentioned in conclusion that crosslinking, capping and internalization of the relevant markers may occur due to the binding of antibodies. Cell function may be restricted thereby. Even if Fab fragments are used, the relevant markers are masked and may in some circumstances have their function impaired. Binding to particular markers may also lead to deactivation of the cell (CD28, go3), induce apoptosis (crosslinking of CD4 in activated cells) or induce the secretion of cytokines (CD3, CD2, CD28). It has not to date been possible in the prior art to carry out any specific identification and/or separation of exclusively living regulatory T cells. The only specific marker FoxP3 described to date may moreover, according to recent investigations, be induced also in non-regulatory T cells (Fontenot J. D. 2003, Hori S. et al. 2003). Since FoxP3 is present as intracellular protein, it is not possible moreover according to the present state of the art to identify and/or isolate living regulatory cells for example on the basis of a FoxP3 antibody. A problem which in turn arises additionally is that only the totality of the Treg can be identified, but not Treg specific for predefined antigens. A reliable identification and/or separation of Treg and in particular antigen-specific Treg has therefore not been possible.

Thus, BD Pharmingen TM: "Technical Data Sheet: PE conjugated mouse anti-human CD137 (4-1BB)", 7 May 2005, also discloses that the 4-1BB marker represents an activation marker for all T cells. WO 2005/124346 also merely describes 4-1BB as being markers on CD4$^+$CD25$^+$; however, the publication does not disclose that CD4$^+$CD25$^+$ specifically express at a particular time during activation 4-1BB markers by comparison with CD4$^+$CD25$^-$T cells. The particular time can be ascertained for example by checks, preferably regular checks. It is possible for example for a sampling or a direct observation to take place at essentially 30-minute intervals to find whether the activated regulatory Th cells have expressed the marker as discriminatory marker. The plurality of, preferably regular, checks are accordingly regular observations of the system, directly by a skilled worker or with the aid of analytical instruments or mechanisms at intervals of 5, 10, 15, 30, 45 minutes, preferably one-hourly intervals. It is thus to determine through the checks the time at which only the activated regulatory cells activate the receptor/marker, it being surprising that this takes place within a short period, preferably of about 0-12 hours, particularly preferably in a period of about 0.5-10 hours and very particularly preferably in a period of about 3-8 hours, especially in substantially or approximately 4 hours. These indications of time relate to the laboratory conditions customary to the skilled worker for activating T cells. If distinctly higher or lower or else or lower temperatures are chosen, or else additions which inhibit or stimulate activation are put in the system, the period may be lengthened or else shortened. Simple determination of the specific timing of expression is possible by for example the skilled worker checking the production of the marker/receptor. The skilled worker of course knows that when T cells are removed from in vivo systems there are always some cells in a cell mixture which are already activated and accordingly produce 4-1BB (receptor). The authors of WO 2005/124346 disclose on the other hand that both cell populations of CD4$^+$CD25$^+$and CD4$^+$CD25$^-$T cells express 4-1BB markers to the same extent after activation thereof. The documents mentioned thus represent the opinion in the art, that 4-1BB markers cannot be used as discriminatory markers for CD25$^+$Treg cells by comparison with CD25$^-$T cells. In particular, BD Pharmingen TM describes a PE-conjugated mouse anti-human CD137 antibody. WO 2005/124346 discloses in particular the costimulation of freshly isolated CD4$^+$CD25$^+$mouse Treg cells via the 4-1BB receptor. The Treg cells are not stimulated via the 4-1BB receptor but via the presence of strong activating stimuli such as CD3. A skilled worker assumes on the basis of the disclosures mentioned that most of the so-called fresh Treg cells do not express 4-1BB. Thus, for example, it is shown in FIG. 5 of WO 2005/124346 that costimulation with 4-1BBL exerts activating properties in particular also on CD25$^-$cells. It is unambiguously disclosed in FIG. 1D that CD4$^+$CD25$^+$and CD4$^+$CD25$^-$T cells both express the 4-1BB receptor during activation, so that the publications mentioned do not motivate the skilled worker to use 4-1BB receptors for specific presentation or isolation of CD4$^+$CD25$^+$Treg cells from cell mixtures.

A method by which live, activated regulatory Th cells (Treg) can be identified and/or isolated has surprisingly been found according to the invention, where the 4-1BB receptor is used as marker and 4-1BB-specific antibodies are used for identifying and/or isolating the activated regulatory T cells.

The invention therefore relates to the surprising teaching that in particular antigen-specifically activated CD4$^+$ CD25$^+$ Treg can be isolated from practically, in particular activated CD4$^+$ CD25$^-$ cells by means of the 4-1BB receptor. By contrast, it is regularly emphasized in the prior art that 4-1BB is an activation marker for CD4$^+$ CD25$^+$ and for CD4$^+$ CD25$^-$ T cells. Especially because none of the abovementioned prior art publications discloses or suggests a specific expression of 4-1BB on CD4$^+$ CD25$^+$ Treg.

The regulatory cells can be identified and/or separated through the expression of one and/or more markers. It is possible to employ for this purpose all markers known to the skilled worker for identification and/or separation. Preferred markers are 4-1BB, CD25, CTLA-4 (cytotoxic T lymphocyte antigen-4), GITR (glucocorticoid-induced TNF receptor), FoxP3, IL-10, CD69, CD40L, ICOS, OX40 and TGFbeta, which are employed singly and/or in combination. It is possible for this purpose also to employ all markers known to the skilled worker for exclusion or depletion of non-regulatory cells in combination. However, it is particularly preferred to use the 4-1BB receptor as marker of live, activated regulatory cells. Either directly activated regulatory T cells are identified or separated, or the activation is induced by adding cells, proteins, peptides, pathogens or other substances.

In a further aspect, the invention relates to the surprising teaching that in particular within a time dependency 4-1BB is a specific marker for activated Treg cells, especially in a period of 0.5 to 18 hours, preferably 0.5 to 12 hours, particularly preferably 0.5 to 10 hours, very particularly preferably between 0.5 and 8 hours, in particular in a period of 3 to 8 hours; especially at a temperature of 37° C. It is possible in a preferred embodiment for 4-1BB to serve as specific marker for separating and isolating the abovementioned cells (activated Treg) through the time-dependent observation of the cells within time units—i.e. the invention relates in a preferred embodiment to the surprising teaching that activated regulatory Th cells can be identified and/or separated, especially if a time-dependent observation is carried out, during which the 4-1BB receptor can be used to isolate CD4$^+$ CD25$^+$ Treg from cell mixtures. The time-dependent observation of the cells makes it possible in particular to use 4-1BB as discriminatory marker for CD25$^+$ Treg by comparison with CD25$^-$ T cells. Although numerous parameter determinations take place time-dependently in the prior art, it is surprising by comparison with the prior art that expression of the marker occurs so asymmetrically within a cell culture in the abovementioned preferred time periods that this marker can be used to identify or separate activated regulatory Th cells (Treg). The use of 4-1BB as specific marker for CD25 Treg has appeared to be precluded to date. Thus, for example, WO 2005/124346 does not disclose that 4-1BB receptors constitute a very specific signature which in fact makes direct isolation possible. The duration of the incubation, especially over a period of 3 to 8 hours, preferably 4 hours allows 4-1BB to be used as discriminatory marker for Treg. This teaching leads in a different direction than the whole prior art. The average skilled worker is able through the disclosure of the teaching of the invention to modify it and extend it to equivalent uses. For example, he will appreciate that the activation also over a period of 18 hours if particular inhibitors are added to the system. If, for example, an addition which prevents regulatory T cells being activated is added to the system, then the period of activation would be longer than 18 hours. Within this system, the skilled worker would recognize a period of over 18 hours as equivalent to 18 hours without an addition which prevents activation of regulatory T cells. The skilled worker will understand the teaching according to the application to mean that the cells are activated. This applies for example to in vitro experiments. However, the skilled worker is aware that some cells may always be activated in in vivo systems. For example, some cells taken for example from a rheumatic inflammatory focus would always be activated, so that cells with regulatory activity are present in a corresponding sample. The skilled worker is also aware that, for example, Treg isolated directly from lymphatic tissue (e.g. in experiments with mouse cells in which the cells are in principle prepared from the spleen) a small part of the isolated Treg shows weak expression of 4-1BB, whereas no 4-1BB expression is detectable with Treg derived from peripheral blood. However, the skilled worker recognizes the equivalence of the in vitro and the in vivo systems. The Treg must preferably be activated for example in vitro, but the skilled worker would not interpret this teaching to mean that this is also the case with selected cells if the Treg are isolated directly from an inflamed sample material. It is conceivable in such a situation for the cells to be isolated without activation directly on the basis of their 4-1BB expression. Assuming that the Treg have been activated directly at the site of the inflammation in vivo, it is preferred for such cells to be isolated, to be expanded in vitro and to be reinfused for therapy for example for inflammations with associated chronic autoimmunity. Realization of the timing of expression of a discriminatory marker especially in a period of approximately or substantially 0.5 to 8 hours of an activation for example in in vitro cultures or of an equivalent period in in vivo cultures, taking account of the fact that some activated cells are regularly present here, makes it possible for the skilled worker to isolate antigen-specific $CD25^+$ regulatory Th cells. Depending on the temperature of the system, the period may vary from approximately 0 to 18 hours, preferably approximately 0.5 to 12 hours, particularly preferably from approximately 0.5 to 10 hours, very particularly preferably from approximately 0.5 to 8 hours, especially in a period of approximately 3 to 8 hours, preferably approximately 4 hours. For example to less than approximately 0.5 hours or distinctly more than approximately 12 or approximately 18 hours.

The separated cells can be picked up and/or collected in any appropriate container, e.g. a collecting tube—which makes it possible for the cells to survive and/or grow. Various media are commercially available and can be used depending on the nature of the identified and/or separated cells. These media may be for example dMEM, HBSS, dPBS, RPMI, Iscove's medium etc., which are frequently supplemented with fetal calf serum, human serum or serum substitutes.

The identified and/or separated cell populations can be used immediately or be cultured in vitro after isolation. Following this, the cells can be frozen, or they are frozen before the separation method. If the cells are stored for a prolonged period, it is preferred to freeze them at temperatures around −80° C. or in liquid nitrogen in order to guarantee that they can be used again after thawing. In this connection, the cells are normally stored in DMSO and/or FCS/HS in conjunction with a medium, glucose etc. As soon as the cells have been thawed they can be used either directly for therapeutic purposes or in vitro experiments or be grown and/or differentiated through the use of growth factors, antigens, cells etc.

It is preferred to identify and isolate the regulatory Th cells from a cell mixture. The regulatory Th cells are identified and/or separated from cell samples from mammals (Mamalia), but especially from humans and preferably from healthy subjects and/or patients. The cell samples can be derived for example from blood samples which contain immune cells (peritoneal, cerebral-spinal, pleural and/or synovial fluid), lavage fluids from hollow organs (airways, lungs), homogenates and aspirates of lymph nodes, spleen, tonsils and/or other lymphatic tissue. The cells can be obtained from animal tissues (e.g. from the spleen or the lymph nodes of an animal). The cells may also be part of a blood sample, e.g. from a test subject or human patient, particularly preferably from a peripheral blood sample.

A further preferred embodiment provides for identification and/or separation of activated regulatory Th cells.

Activated regulatory Th cells are directly able to suppress the activity of T cells. It has been shown in animal models that activated regulatory T cells can prevent the development of autoimmune diseases, of transplant rejection reactions and allergic reactions. It is assumed in analogy thereto that activated regulatory T cells may also prevent the development of chronic immune responses in humans. Activated regulatory Th cells are specifically identified and/or separated through use of the 4-1BB marker. Regulatory Th cells which have previously been activated in vitro and have the phenotype CD4+ CD25+ FoxP3+ are preferably identified and/or separated. The activation takes place in this case preferably by means of antigens, antibodies, peptides, proteins, chemical compounds (or mixtures of such substances) or pathogens or cells. A further particular embodiment of the invention is the direct ex vivo identification and/or isolation of live regulatory Th cells.

It is possible through use of the 4-1BB marker and the corresponding 4-1BB antigen preferably to identify and/or separate activated regulatory Th cells, thus permitting a preferred use of the invention for identifying and/or isolating antigen-specific regulatory Th cells.

After a cell mixture has been obtained from a patient and/or subject, stimulation with particular antigens thereof is possible. It is possible to use for this purpose antibodies, peptides, proteins, chemical compounds (or mixtures of such substances) or pathogens or cells. After a particular activation time, the regulatory Th cells are identified and/or separated through the use of the 4-1BB marker. In this case, antigen-specific regulatory Th cells are preferably identified and/or separated.

The cells separated according to the invention generally originate from an in vivo source and therefore reflect the immunological status of the donor in relation to the number, the location and the T-cell antigen receptor specificity of the Treg cells again. This information can be used in diagnostic tests related to immunological impairments, e.g. cancer-related immunosuppression, autoimmune disorders; atopic conditions, etc.

A further possibility is for Th cells of the target patient to be exposed in vitro to cells, cell extracts, separated antigens or proteins of the organ donor before or after transplantation. After this, the active regulatory Th cells would, after an appropriate activation time, be identified and/or separated on the basis of the 4-1BB marker.

The cells can be identified and/or separated by all techniques known to the skilled worker. The methods suitable and preferred for identifying the cells are magnetic cell sorting (MACS), fluorescence-activated cell sorting (FACS), ELISA, PCR and/or all fluorescence microscopes known to the skilled worker. Flow cytometry (FACS) is particularly preferably suitable. The cells-separation systems suitable and preferred for separating the cells are those by which the cells are sorted with the aid of a magnetic field (MACS) or by flow cytometry (FACS). It is preferred to measure the expression of the 4-1BB receptor after stimulation.

The regulatory Th cells are stimulated by substances known to the skilled worker. The expression of the 4-1BB receptor is measured after stimulation for 1 h to 18 h. The expression is preferably measured after stimulation for 3 h to 8 h.

The preferred optimal stimulation time is the time at which the maximum number of activated, regulatory T cells but the minimum number of non-regulatory cells express 4-1B. This time can be ascertained by the skilled worker by analyzing 4-1BB expression at various times after stimulation.

A further preferred embodiment provides for the regulatory Th cells to be identified and/or separated after stimulation of the cells in the cell mixture.

A further preferred use of the invention is to stimulate the cells by antigens, proteins, peptides, chemical substances, cells, growth factors, antibodies and/or ligands.

The culture may additionally comprise suitable growth factors. Growth factors are defined as molecules which promote the survival, growth and/or differentiation of a cell whether in culture or in intact tissue by particular effects on a transmembrane receptor. Growth factors include polypeptides and non-polypeptide factors. Particular growth factors which can be used to culture the separated and/or used cell include the interleukins, e.g. IL-1, IL-2, IL-3, IL-4, IL-5, IL-6, IL-7, IL-8, IL-8, IL-10, IL-11, IL-12, IL-13, IL-14, IL-15, IL-16, IL-17, IL-18 etc.; antigens, e.g. peptide antigens, protein antigens such as, for example, alloantigens, preferably in conjunction with cells showing antigens, lectins, e.g. ConA, [alpha]-CD3, LPs, etc.

The culture may also comprise antibodies or specific ligands (purified ligands, FC fusion proteins or other recombinant forms of the leucine zipper) for cell surface receptors which are able to stimulate or inhibit Treg activity. The medium may also comprise mAb or ligands which bind TNFR or other costimulating molecules on Treg and stimulate and/or increase Treg activity, abolish Treg activity (and bring about growth), or stimulate apoptosis of the Treg. It is normally desired that the specific culture conditions serve a particular purpose, e.g. maintenance of Treg cell activity etc.

It is preferred to use antibodies for detecting the 4-1BB receptor.

The 4-1BB antibodies are added to a cell suspension and incubated for a sufficient time in order to bind the available cell surface antigens. The incubation normally amounts to at least about 5 minutes up to 18 h. Expression is measured after stimulation for 3 h to 8 h. The optimal incubation time is that within which a maximum number of the activated, regulatory T cells but a minimum number of non-regulatory cells are 4-1B labeled. This time can be ascertained by the skilled worker by analyzing incubation times of various lengths during or after the stimulation. It is desirable to have an adequate concentration of antibodies in the reaction mixture, so that the efficiency of separation is not limited by an antibody deficiency. The appropriate concentration can also be determined by titration.

The composition in which the cells are separated can be any composition which maintains the activity of the cells. A preferred composition is a phosphate-buffered saline solution which comprises 0.1 to 0.5% BSA or in equal proportions autologous, pooled serum or serum substitutes. Various media are commercially available and can be used depending on the cell type and the experiment. Available media are Dulbecco's modified Eagle's medium (dMEM), Hank's basic salt solution (HBSS), a Dulbecco's phosphate-buffered saline solution (dPBS), RPMI, Iscove's medium, PBS with 5 mM EDTA etc., frequently supplemented by fetal calf serum BSA, HSA, etc.

The characterized cells are then separated depending on the expression of 4-1BB. The separated cells can be collected in any appropriate composition which maintains the viability of the cells. They are normally collected in a collecting tube with some serum. Various media are commercially available and can be used depending on the nature of the identified and/or separated cells, e.g. dMEM, HBSS including, dPBS, RPMI, Iscove's medium etc., frequently supplemented with fetal calf serum, autologous or pooled serum or serum substitutes.

It is further preferred for the antigens for detecting the 4-1BB receptor to be coupled to a fluorescent substance or directly to magnetic microparticles.

The antibodies employed for flow cytometry or FACS (fluorescence activated cell sorting) and magnetic cell sorting or MACS (magnetic activated cell sorting) may be coupled to fluorescent markers or magnetic microparticles which are known to the skilled worker, such as, for example, FITC, phycoerythrin (PE), allophycocyanin (APC), cascade yellow and peridinin chlorophyll protein (PerCP). The antibodies may also be coupled to haptens and then to be detected with hapten-specific secondary antibodies. A combination of antibodies can be used to detect, analyze and/or isolate different cells with different properties on the basis of markers such as, for example, secretory proteins or characteristic surface molecules. It is possible in particular to employ fluorecence-labeled antibodies for FoxP3, CD25 and/or CD4 markers. It is possible particularly preferably to employ 4-1BB antibodies which are fluorescence-labeled or coupled to magnetic microparticles. Magnetic microparticles may in this case be used directly or indirectly (hapten e.g. biotin and anti-hapten microparticles or fluorochromes, e.g. PE or APC and anti-fluorochrome microparticles).

A further preferred embodiment provides for the regulatory Th cells to be directly identified and/or separated or isolated from blood, peripheral mononuclear blood cells (PBMC), body tissue or cells of tissue fluid.

The regulatory Th cells are normally identified and/or separated from cell samples from mammals (Mamalia), but especially from humans and preferably from test subject and/or patients. The regulatory Th cells may be derived for example from blood samples which comprise immune cells (peritoneal, cerebral-spinal, pleural and/or synovial body fluids, lavage fluids from hollow organs (airways, lungs), homogenates and aspirates of lymph nodes, spleen, tonsils and/or other lymphatic tissue. The regulatory Th cells may also be obtained from animal tissues (e.g. from the spleen or the lymph nodes of an animal). The Th cells may also be part of a blood sample, e.g. from a test subject or human patient, particularly preferably from peripheral mononuclear blood cells (PBMC), body tissue or cells of tissue fluid.

The invention provides a kit comprising an antibody for detecting the 4-1BB receptor for identifying and/or separating a regulatory Th cell.

It is preferred for the 4-1BB receptor antibody in the kit to be coupled to a fluorescent substance, to a hapten or to magnetic microparticles.

A 4-1BB receptor antibody which is coupled to a fluorescent marker, a hapten or magnetic microparticles is provided for identifying and/or separating the activated, live regulatory Th cells. Fluorescent markers are known to the skilled worker, such as, for example, FITC, phycoerythrin (PE), allophycocyanin (APC), cascade yellow and peridinin chlorophyll protein (PerCP).

A preferred property of the kit is further that activated regulatory Th cells are identified and/or separated.

It is possible through use of the kit comprising a 4-1BB receptor antibody coupled to a fluorescent marker, haptens or magnetic microparticles to identify and/or separate regulatory Th cells. It is possible through the use of the 4-1BB receptor antibody preferably to identify and/or separate activated regulatory Th cells. Live, activated regulatory Th cells are particularly preferably identified and/or separated.

In this embodiment, the method of the invention can be used for example to identify and/or separate Th cells from a blood sample (or from a blood derivative) or from cell mixture derivatives of lymphatic organs or tumors of mammals.

The separated regulatory Th cells can be used before and/or after cloning and/or growing and/or concentrated in cell mixtures in and/or as pharmaceutical composition in the therapy or prevention of diseases. It is additionally possible for the coding gene sequences of the TCR (T-cell receptor) to be isolated from the separated regulatory T cells and be used for further therapeutic purposes such as, for example, for cancer therapies. It is additionally possible to employ the regulatory Th cells in the form mentioned in further investigations and/or analyses. The pharmaceutical composition can be used for the treatment and/or prevention of diseases in mammals, possibly including administration of a pharmaceutically effective amount of the pharmaceutical composition to the mammal.

The disease may be any disease which can be treated and/or prevented through the presence of a separated cell and/or through increasing the concentration of the relevant cells in/at the relevant place, or in whole mammalian subjects and/or patients. The cell may be for example a regulatory Th cell, and the treated and/or preventively treated disease may be an autoimmune disease, an infectious disease, an allergy, transplant versus host disease (or allogeneic transplant rejection) and/or any other disease initiated by hypersensitivity.

Diseases for which the use set forth in the invention is particularly suitable are those arising through and/or during a lack of regulation of the immune response. These diseases may be transplant rejections, allergic conditions, certain infectious diseases and/or autoimmune diseases.

It is known in connection with autoimmune diseases that the immune system attacks endogenous structures, such as, for example, in rheumatoid arthritis, insulin-dependent Diabetes mellitus (IDDM), multiple sclerosis (MS), atherosclerosis, psoriasis, allogeneic stem cell transplantation, organ transplantation. A therapy with specific regulatory T cells is advantageous here. The intention in neoplastic diseases is to eliminate regulatory T cells specific for tumor antigens so that the immune system can initiate efficient anti-tumor immune responses.

The invention also relates to the use of the composition of the invention and/or of the pharmaceutical composition of the invention for the treatment of diseases which are associated with a deficiency of cellular immunity, for example in the defect according to ICDIO code: D.84.4. Possibilities in this connection are septic disorders, inflammatory reactions and fever, autoimmune diseases and diseases of impairment of cell division such as, for example, cancer.

Inflammations in the sense of the invention are the reaction, borne by the connective tissue and the blood vessels, of the body to an externally or internally induced inflammatory stimulus with the purpose of eliminating or inactivating it and repairing the stimulus-related tissue damage. Inducing effects are exerted by mechanical stimuli (foreign bodies, pressure, injury) and other physical factors (ionizing radiation, UV light, heat, cold), chemical substances (alkalis, acids, heavy metals, bacterial toxins, allergens and immune complexes) and pathogens (microorganisms, worms, insects) and pathological metabolic products, dysfunctional enzymes, malignant tumors. The event starts with a brief arteriolar constriction (through the action of adrenaline) with inadequate blood flow and tissue alteration, followed by the development of the classical local signs of inflammation (cardinal symptoms; according to GALEN and CELSUS), i.e. of redness (=rubor; dilation of vessels due to histamine), warmth (=calor; through a local increase in metabolism), swelling (=tumor; through escape of protein-rich liquid from the vessel walls which are altered—inter alia by histamine—, assisted by the slowed circulation of blood in the sense of prestasis to stasis), pain (=dolor; as a consequence of the increased tissue tension and pain-inducing inflammatory products, for example bradykinin) and functional impairment (=functio laesa). The process is supplemented by disturbance of the electrolyte balance (transmineralization), invasion of neutrophilic granulocytes and monocytes through the vessel walls (see also leukotaxis), the latter with the purpose of eliminating the inflammatory stimulus and damage to necrotic cells (phagocytosis); there is also invasion of lymphocyte effector cells which lead to the production of specific antibodies against the inflammatory stimulus (immune response), and eosinophils (in the healing phase or—very early—in the allergic-hyperergic event). The activation of the complement system brought about by the reaction releases fragments (C3a and C5a) of this system which—like histamine and bradykinin—act as mediators of the inflammation, specifically in the sense of stimulating the chemotaxis of the cited blood cells; there is also activation of blood clotting. This is followed by damage (dystrophy and coagulation necrosis) of the relevant organ parenchyma. The whole body responds depending on the intensity and nature of the inflammation with fever, stress (see also adaptation syndrome), leucocytosis and alterations in the composition of plasma proteins (acute-phase reaction) which lead to an increased erythrocyte sedimentation rate. Preferred inflammations in the sense of the invention are the purulent, the exudative, the fibrinous, the gangrenous, the granulomatous, the hemorrhagic, the catarrhal, the necrotic, the proliferative or productive, the pseudomembranous, the serous, the specific or the ulcerative inflammations.

Autoimmune disease in the sense of the invention are diseases partly attributable to the production of autoantibodies and their harmful effect on the whole body or organ systems, i.e. autoaggression. Autoimmune diseases may on the other hand also be diseases in which T cells possess a predominant role in the pathogenesis or initiation. Classification as organ-specific, intermediary and/or systemic autoimmune diseases is possible. Preferred organ-specific autoimmune diseases are Hashimoto's thyroiditis, primary myxedema, thyrotoxicosis (Basedow's disease), pernicious anemia, Addison's disease, myasthenia gravis and/or juvenile diabetes mellitus. Preferred intermediary autoimmune diseases are Goodpasture's syndrome, autoimmune hemolytic anemia, autoimmune leucopenia, idiopathic thrombocytopenia, pemphigus vulgaris, sympathetic ophthalmia, primary biliary cirrhosis, autoimmune hepatitis, ulcerative colitis and/or Sjögren's syndrome. Preferred systemic autoimmune diseases are rheumatoid arthritis, rheumatic fever, systemic lupus erythematosus, dermatomyositis/polymyositis, progressive systemic sclerosis, Wegener's granulomatosis, panarteritis nodosa and/or hypersensitivity angiitis. Typical autoimmune diseases are thyrotoxicosis, thyroid-related myxedema, Hashimoto's thyroiditis, generalized endocrinopathy, pernicious anemia, chronic gastritis of type A, diseases of single or all corpuscular elements of the blood (for example autoimmune hemolytic anemia, idiopath. thrombocytopenia or -pathy; idiopath. leucopenia or agranulocytosis), pemphigus vulgaris and pemphigoid, sympathetic ophthalmia and some types of uveitis, primary biliary cirrhosis of the liver and chronic aggressive autoimmune hepatitis, diabetes mellitus of type I, Crohn's disease and ulcerative colitis, Sjögren's syndrome, Addison's disease, lupus erythematosus disseminatus and as discoid form of this disease, as dermatomyositis and scleroderma, rheumatoid arthritis (=primary chronic polyarthritis), antiglomerular basement membrane nephritis. An aggressive immune response as a result of collapse of immunotolerance of self determinants and a preponderance of inflammatory T-helper cells are the basis. The production of autoantigens is also possible, for example through host proteins combining with haptens (for example drugs), through ontogenetic tissue which develops only after development of self tolerance and for protein components unmasked through changes in the conformation of the proteins in connection for example with infection by viruses or bacteria; also for new proteins which have arisen in connection with neoplasms first.

Septic diseases in the sense of the invention are disorders resulting from continuous or periodic invasion of pathogenic bacteria and/or their toxins from a disease focus and spread thereof via the lymph and blood to general or local infection. Sepsis in the sense of the invention are preferably wound sepsis (phlegmone, thrombophlebitis, lymphangitis), puerperal sepsis (in puerperal fever), otogenic sepsis (in otitis media), tonsillogenic sepsis (in angina, peritonsilitis), cholangitic sepsis (in purulent cholecystitis, cholangitis), pylephlebitic sepsis (in pylephlebitis), umbilical sepsis (in omphalitis etc.), urosepsis and in dental granuloma. Sepsis in the sense of the invention may occur acutely to highly acutely (foudroyantly), subacutely (for example as endocarditis lenta) or chronically, but of course also as neonatal sepsis. Sepsis in the sense of the invention are therefore all pathogenic alterations in a patient which may be associated with intermittent fever and chills, and with spleen tumor, with toxic reactions or damage of the bone marrow or blood (polynuclear leukocytosis, anemia, hemolysis, thrombocytopenia) or else with pathogenic reactions on the heart and vasomotor nerves (tachycardia, centralization of the circulation, edema, oliguria; possibly shock) or of the digestive tract (dry, coated tongue, diarrheas) or else with septicopyemia (pyemia with formation of septic infarctions and metastatic abscess).

Preferred disorders which are associated with a deficiency of the cellular immune system are in the sense of the invention also:
AIDS, acne, albuminuria (proteinuria), alcohol withdrawal syndrome, allergies, alopecia (hair loss), ALS (amyotrophic lateral sclerosis), Alzheimer's disease, AMD (age-related macular degeneration), anemia, anxiety disorders, anthrax, aortic sclerosis, arterial occlusive disease, arterial calcification, arterial occlusion, temporal arteritis, arteriosclerosis, arteriovenous fistulas, arthritis, arthrosis, asthma, respiratory failure, autoimmune disease, AV block, acidosis, prolapsed disc, peritonitis, pancreatic cancer, Becker's muscular dystrophy, benign prostatic hyperplasia (BPH), bladder carcinoma, hemophiliac, bronchial carcinoma, breast cancer, BSE, Budd-Chiari syndrome, bulimia nervosa, bursitis, Byler syndrome, bypass, chlamydial infection, chronic pain, cirrhosis, concussion, Creutzfeld-Jakob disease, bowel carcinoma, bowel cancer, intestinal tuberculosis, depression, diabetes insipidus, diabetes mellitus, diabetes mellitus juvenilis, diabetic retinopathy, Duchenne's muscular dystrophy, duodenal carcinoma, progressive muscular dystrophy, dystrophy, ebola, eczema, erectile dysfunction, obesity, fibrosis, cervical cancer, uterine cancer, cerebral hemorrhage, encephalitis, hair loss, hemolytic anemia, hemophilia, pet allergy (animal hair allergy), skin cancer, herpes zoster, myocardial infarction, heart failure, inflammation of heart valves, cerebral metastasis, stroke, brain tumor, testicular cancer, ischemia, Kahler's disease (plasmocytoma), infantile paralysis (poliomyelitis), bone atrophy, contact eczema, paralysis, cirrhosis of the liver, leukemia, pulmonary fibrosis, lung cancer, pulmonary edema, lymph node cancer (Hodgkin's disease), lymphogranulomatosis, lymphoma, lyssa, gastric carcinoma, carcinoma of breast, meningitis, anthrax, mucoviscidosis (cystic fibrosis), multiple sclerosis (MS), myocardial infarction, neurodermatitis, neurofibromatosis, neuronal tumors, renal cancer (renal cell carcinoma), osteoporosis, pancreatic carcinoma, pneumonia, polyneuropathies, potency impairments, progressive systemic sclerosis (PSS), prostate cancer, urticaria, transverse syndrome, traumatic, rectal carcinoma, pleurisy, craniocerebral trauma, vaginal cancer (vaginal carcinoma), sinusitis, esophageal cancer, tremor, tuberculosis, tumor pain, vaginal carcinoma, burns/scalds, poisonings, viral meningitis, menopause, soft tissue sarcoma, soft tissue tumor, impairments of cerebral blood flow and/or CNS tumors.

In a preferred embodiment, the cancer or the tumor which is treated or prevented is selected from the group of cancers or neoplastic diseases of the ear/nose/throat region, of the lung, of the mediastinum, of the gastrointestinal tract, of the urogenital system, of the gynecological system, of the breast, of the endocrine system, of the skin, bone and soft tissue sarcomas, mesotheliomas, melanomas, neoplasms of the central nervous system, cancers or neoplastic diseases in childhood, lymphomas, leukemias, paraneoplastics syndromes, metastases without known primary tumor (CUP syndrome), peritoneal carcinomatoses, immunosuppression-related malignancies and/or tumor metastases.

The tumors may be in particular of the following types of cancer: adenocarcinoma of the breast, of the prostate and of the colon; all types of lung cancer derived from the bronchia; bone marrow cancer, melanoma, hepatoma, neuroblastoma; papilloma; apudoma, choristoma, branchioma; malignant carcinoid syndrome; carcinoid heart disease; carcinoma (for example Walker's carcinoma, basal cell carcinoma, basosquamous carcinoma, Brown-Pearce carcinoma, ductal carcinoma, Ehrlich's tumor, carcinoma in situ, Krebs-2carcinoma, Merkel cell carcinoma, mucous carcinoma, non-small cell bronchial carcinoma, oat cell carcinoma, papillary carcinoma, scirrhous carcinoma, bronchiole-alveolar carcinoma (bronchial carcinoma, squamous cell carcinoma and transitional cell carcinoma); histiocytic dysfunction; leukemia (for example in connection with B-cell leukemia, mixed cell leukemia, null cell leukemia, T-cell leukemia, chronic T-cell leukemia, HTLV II-associated leukemia, acute lymphocytic leukemia, chronic lymphocytic leukemia, master cell leukemia and myeloid leukemia); malignant histiocytosis, Hodgkin's disease, non-Hodgkin lymphoma, solitary plasma cell tumor; reticuloendotheliosis, chondroblastoma; chondroma, chondrosarcoma; fibroma; fibrosarcoma; giant cell tumors; histiocytoma; lipoma; liposarcoma; leukosarcoma; mesothelioma, myxoma, myxosarcoma; osteoma; osteosarcoma; Ewing's sarcoma; synovioma; adenofibroma; adenolymphoma; carcinosarcoma, chordoma, craniopharyngioma, dysgerminoma, hamartoma; mesenchymoma; mesonephroma, myosarcoma, ameloblastoma, cementoma; odontoma; teratoma; thymoma, chorioblastoma; adenocarcinoma, adenoma; cholangioma; cholesteatoma; cylindroma; cystadenocarcinoma, cystadenoma; granulose cell tumor; gynadroblastoma; hidradenoma; islet cell tumor; leydig cell tumor; papilloma, sertoli cell tumor, theka cell tumor, leiomyoma; leiomyosarcoma; myoblastoma; myoma; myosarcoma; rhabdomyoma; rhabdomyosarcoma; ependynoma; ganglion-euroma, glioma; medulloblastoma, meningioma; neurilemmonoma; neuroblastoma; neuroepithelioma, neurofibrona, neuroma, paraganglioma, non-chromaffin paraganglioma, angiokeratoma, angiolymphoid hyperplasia with eosinophilia; sclerosieren angiomas; angiomatosis; glomangioma; hemangioendothelioma; hemangioma; hemangiopericytoma, hemangiosarcoma; lymphangioma, lymphangiomyoma, lymphangiosarcoma; pinealoma; cystosarcoma phyllodes; hemangiosarcoma; lymphangiosarcoma; myxosarcoma, ovarian carcinoma; sarcoma (for example Ewing's sarcoma, experimentally, caposi sarcoma and master cell sarcoma); neoplasms (for example bone neoplasms, breast neoplasms, neoplasms of the digestive system, colorectal neoplasms, liver neoplasms, pancreatic neoplasms, pituitary neoplasms, testicular neoplasms, orbital neoplasms, neoplasms of the head and neck, of the central nervous system, neoplasms of the hearing organ, of the pelvis, of the respiratory tract and of the urogenital tract); neurofibromatosis and cervical squamous cell dysplasia.

In a further preferred embodiment, the cancer or the tumor which is treated or prevented is selected from the group: tumors of the ear nose and throat region including tumors of the inner nose, of the paranasal sinuses, of the nasopharynx, of the lips, of the oral cavity, of the oropharynx, of the larynx, of the hypopharynx, of the ear, of the salivary glands and parangliomas, tumors of the lung including non-small cell bronchial carcinomas, small cell bronchial carcinomas, tumors of the mediastinum, tumors of the gastrointestinal tract including tumors of the esophagus, of the stomach, of the pancreas, of the liver, of the gall bladder and of the biliary tract, of the small bowel, colon and rectal carcinomas and anal carcinomas, urogenital tumors including tumors of the kidneys, of the uretas, of the bladder, of the prostate, of the urethra, of the penis and of the testis, gynecological tumors including tumors of the cervix, of the vagina, of the vulva, corpus carcinoma, malignant trophoblastic disease, ovarian carcinoma, tumors of the uterine tube (tuba faloppii), tumors of the abdominal cavity, carcinomas of the breast, tumors of endocrine organs including tumors of the thyroid, of the parathyroid, of the adrenal cortex, endocrine pancreatic tumors, carcinoid tumors and carcinoid syndrome, multiple endocrine neoplasms, bone and soft tissue sarcomas, mesotheliomas, skin tumors, melanomas including cutaneous and intraocular melanomas, tumors of the central nervous system, tumours in childhood including retinoblastoma, Wilm's tumor, neurofibromatosis, neuroblastoma, Ewing's sarcoma tumor family, rhabdomyosarcoma, lymphomas including non-Hodgkin lymphomas, cutaneous T-cell lymphomas, primary lymphomas of the central nervous system, Hodgkin's disease, leukemias including acute leukemias, chronic myeloid and lymphatic leukemias, plasma cell neoplasms, myelodysplastic syndromes, paraneoplastic syndromes, metastases without known primary tumor (CUP syndrome), peritoneal carcinomatosis, immunosuppression-related malignancy including AIDS-related malignancies such as Kaposi's sarcoma, AIDS-associated lymphomas, AIDS-associated lymphomas of the central nervous system, AIDS-associated Hodgkin's disease and AIDS-associated anogenital tumors, transplantation-related malignancies, metastatic tumors including brain metastases, lung metastases, liver metastases, bone metastases, pleural and pericardial metastases and malignant ascites.

In a further preferred embodiment, the cancer or the tumor which is treated or prevented is selected from the group including cancers or neoplastic diseases of the carcinomas of the breast, of the gastrointestinal tumors, including colon carcinomas, gastric carcinomas, pancreatic carcinomas, colon cancer, small bowel cancer, of the ovarian carcinomas, of the cervical carcinomas, lung cancer, prostate cancer, renal cell carcinomas and/or liver metastases.

Immunopathological reactions cause the loss of function of a particular tissue and may destroy tissues. The use according to the invention allows active regulatory Th cells to be isolated from patients with these diseases in order to treat the tissue-damaging immune response. In the case of neoplastic diseases, the use according to the invention is intended to make it possible to specifically eliminate tumor-specific Treg in vitro or ex vivo. If the regulatory Th cells are present in too small a number, they can be separated and concentrated and/or grown in cell cultures. In both cases, the patient could be treated with the concentrated and/or grown and thus increased number of regulatory Th cells, which would lead to the expectation of suppression of the immunopathological response and thus an improvement and/or cure of the disease. Autoimmune diseases for which the 4-1BB receptor could be used as marker for identifying and/or isolating and subsequently concentrating active regulatory Th cells and would be expected to be a successful therapy include, but are not restricted only thereto, diabetes mellitus (IDDM), multiple sclerosis (MS), atherosclerosis (AS), psoriasis, inflammations of the bowel, autoimmune-related hemolytic anemia, Sjogren's syndrome, autoimmune-related thyroiditis and systemic lupus erythematosis.

The skilled worker is aware that regulatory Th cells are able in connection with transplantations to suppress an immune responses which might lead to transplant rejection. Treatment of a patient and/or subject with initially isolated and then concentrated specifically activated regulatory Th cells might prevent and/or impede transplant rejection. Transplant rejections are induced by an immune response of the transplant acceptor. In this case, the immune cells of the acceptor attack the exogenous tissue. In this form of use, Th cells of the target patient would be exposed in vitro to cells, cell extracts, isolated antigens or proteins of the organ donor before or after the transplantation. After this, the active regulatory Th cells would, after an appropriate growing time, be identified and/or separated by means of the 4-1BB marker. The identified and/or separated active regulatory Th cells would then be returned to the transplant acceptor. The result thereof is that the cells treated by this method suppress the immune response to the transplant, and the transplant rejection is delayed or prevented. Use of the 4-1BB marker might be employed inter alia for allogeneic transplants and/or heterotransplants such as, for example, for transplantations of the heart, lungs, bowel, cornea, kidneys and bone marrow.

In the case of an allergy, regulatory Th cells would be identified and/or separated either before the polyclonal activation of the T cells or after culturing with specific allergens. The identified and/or separated cells would then be returned, after a possible growing, to the patient. It is then expected that the regulatory Th cells treated in this way will suppress the immune response, and the symptoms correlating with the antigens used will improve.

The treatment of allergies by means of identifying and/or isolating active regulatory Th cells with the 4-1BB marker and the described method would be suitable inter alia for skin rashes, atopic dermatitis, asthma, allergic rhinitis, insect toxins and food allergy such as, for example, toward gluten, dairy products, nuts and/or fish antigens.

In the case of infectious diseases it is important to strengthen the immune response than to weaken it. In certain diseases it is appropriate to modulate the immune response in order to alter the progression of the disease. Such cases of modulation occur in diseases where immunopathological reactions occur through the infection and destroy tissue, and in those where the immune response does not protect the body. It would be possible through the identification and/or isolation of active regulatory Th cells to suppress the immune response and ameliorate and/or prevent immunopathological damage.

A further alternative would be treatment with regulatory Th cells which have been isolated from a patient and exposed to particular antigens in order to obtain regulatory Th cells which could redirect the immune response in a defined, particular direction.

Genes can be introduced into the cells before culturing or transplantation for a diversity of purposes, e.g. in order to prevent or reduce the susceptibility to an infection, to replace genes which are subject to a loss of a functional mutation, to increase the ability of the Treg to inhibit Th cells etc. It is moreover possible to introduce vectors which express antisense mRNA or ribozymes, thus blocking the expression of an unwanted gene. Other methods of gene therapy are the introduction of drug-resistance genes, for example the drug-resistance gene (MDR) or antiapoptosis genes such as bcl-2. A further possibility is to use techniques known to the skilled worker for transfecting target cells, e.g. by electroporation, calcium-precipitated DNA, fusion, transfection or lipofection. The particular way in which the DNA is introduced is not crucial for use of the invention.

The skilled worker is aware of many vectors which can be used in order to transfer exogenous genes into mammalian cells. The vectors may be episomal, e.g. plasmids, virus vectors such as, for example, cytomegalovirus, adenovirus etc. The genes can also be integrated into the target cell genome by homologous recombination or by random integration, such as, for example, vectors derived from retroviruses such as MMLV, HIV-1, ALV, etc.

Active factors of the Treg cells can be analyzed by means of in vitro assays or screenings. It is also possible to carry out coculture assays in order to study the alterations in Tregs which suppress the multiplication of normal T cells including CD4 T and CD8 T. Interactions with dendritic cells and other antigen-determined cells can likewise be investigated. The regulatory cells separated according to the invention can be the starting material for a large diversity of different analyses, e.g. of immunoassays for protein-binding studies, determinations of cell growth, differentiation and functional activity, production of hormones etc.

The figures depict the following:

FIGS. 1a and 1b 4-1BB is expressed specifically by regulatory T cells soon after activation Various subpopulations (I-IV) of peripheral Th cells (A) were isolated from PBMC (B) by FACS, and intracellular analyses of the transcription factor Foxp3 which is specific for regulatory T cells were carried out on aliquots (C). The isolated subpopulations were then stimulated with PMA/ionomycin in vitro for various lengths of time (0, 4 and 8 hours), and expression of 4-1BB was analyzed by FACS (D).

FIG. 2

The transcription factor Foxp3 which is specific for regulatory T cells is specifically expressed in 4-1BB$^+$ Th cells after activation (RNA analysis)

PBMC were stimulated in vitro with the superantigen SEB for 4 h and then 4-1BB$^+$ and 4-1BB$^-$ Th cells were isolated by FACS. RNA was isolated from the isolated cells and the expression of Foxp3 was analyzed by RT-PCR.

FIG. 3

The transcription factor Foxp3 which is specific for regulatory T cells is expressed specifically in 4-1BB$^+$ Th cells after activation (protein analysis)

CD4$^+$ Th cells were isolated from PBMC and stimulated in vitro with PMA/ionomycin for 4 h. 4-1BB$^+$ and 4-1BB$^-$ Th cells were then isolated by FACS. The isolated cells were then labeled intracellularly with Foxp3-specific antibodies.

FIG. 4

Coexpression of 4-1BB and Foxp3 soon after activation

CD4$^+$ Th cells were isolated from PBMC and stimulated in vitro with PMA/ionomycin for 4 h. The cells were then labeled extracellularly with antibodies against CD69 (activation marker) and 4-1BB. This was followed by intracellular labeling with Foxp3-specific antibodies. The left analysis plot indicates the electronic analysis window for CD69$^+$ activated Th cells. The right analysis plot depicts the coexpresson of 4-1BB and Foxp3 in CD69$^+$ activated Th cells.

FIGS. 5 to 7:

Specificity and in vitro suppression of TSST-1-specific CD25$^{++}$ Treg after isolation via TSST-1-induced 4-1BB expression

FIG. 5:

Resting regulatory CD25$^{++}$ CD4$^+$ T cells were isolated from PBMC of a healthy donor by FACS and cultured with autologenous CD4$^-$ CD25$^-$ PBMC in a ratio of 1:2 with 1 µg/ml TSST-1 at 37° C. for 4 h. 4-1BB$^+$ and 4-1BB$^-$ CD4$^+$ CD69$^+$ T cells were then isolated by FACS.

FIG. 6:

4-1BB$^+$ and 4-1BB$^-$ CD4$^+$ CD69$^+$ T cells were labeled directly after FACS sorting with antibodies against Foxp3, Vbeta2 and Vbeta17 and analyzed.

FIG. 7:

4-1BB$^+$ CD4$^+$ CD69$^+$ T cells were cultured after FACS sorting in medium and 10% FCS for 6 days. They were then cultured with CFSE-labeled naïve CD45RA$^+$ CD4$^+$ T cells and CD4$^-$ PBMC in the ratio 1:1:1 in the presence of TSST1 0.5 µg/ml for 4 days. As a control, CFSE-labeled naïve CD45RA$^+$ CD4$^+$ T cells and CD4$^-$ PBMC were cultured in the ratio 2:1 in the presence of TSST1 0.5 µg/ml for 4 days.

Figure 1A:
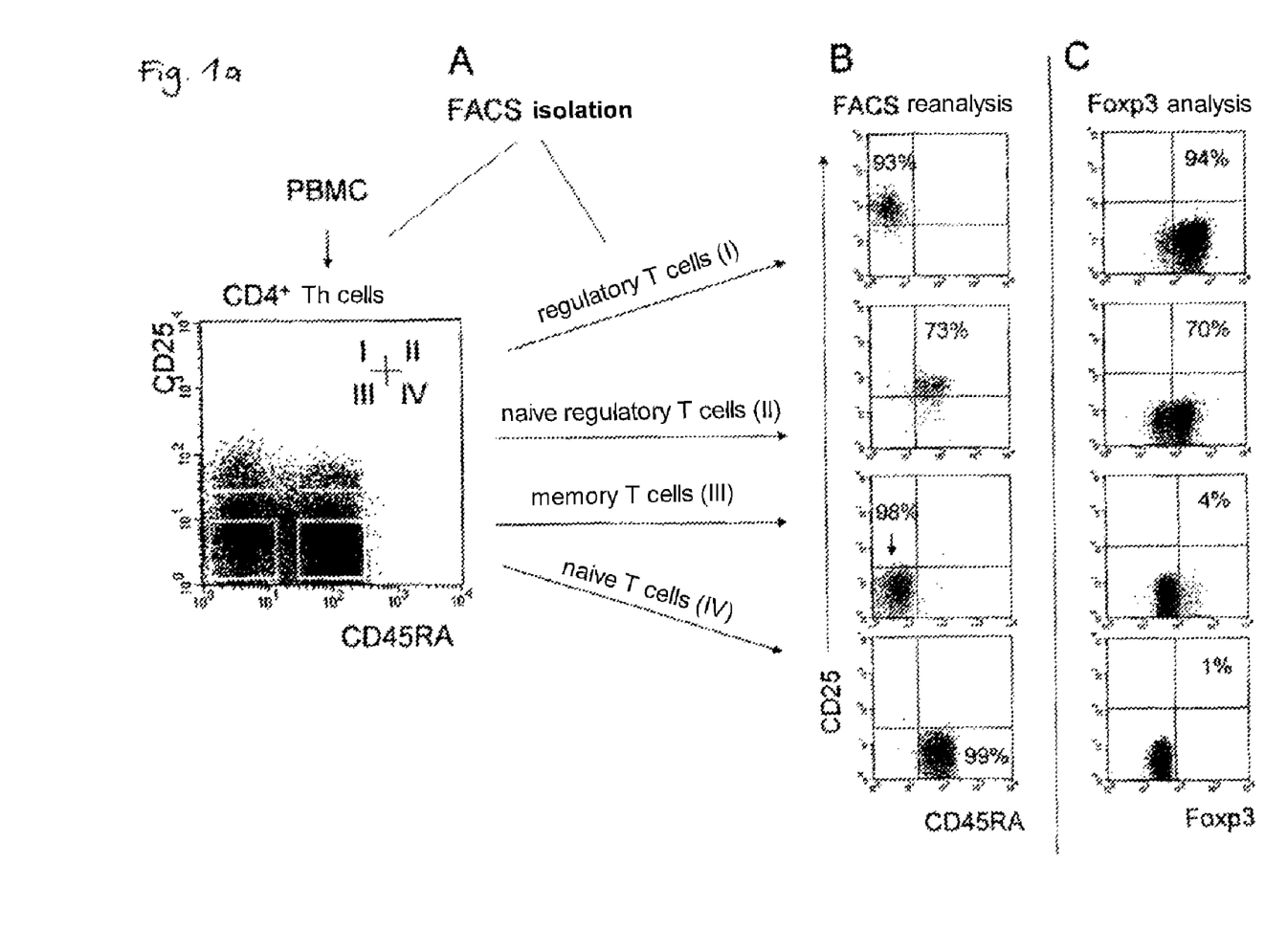
Figure 1B:
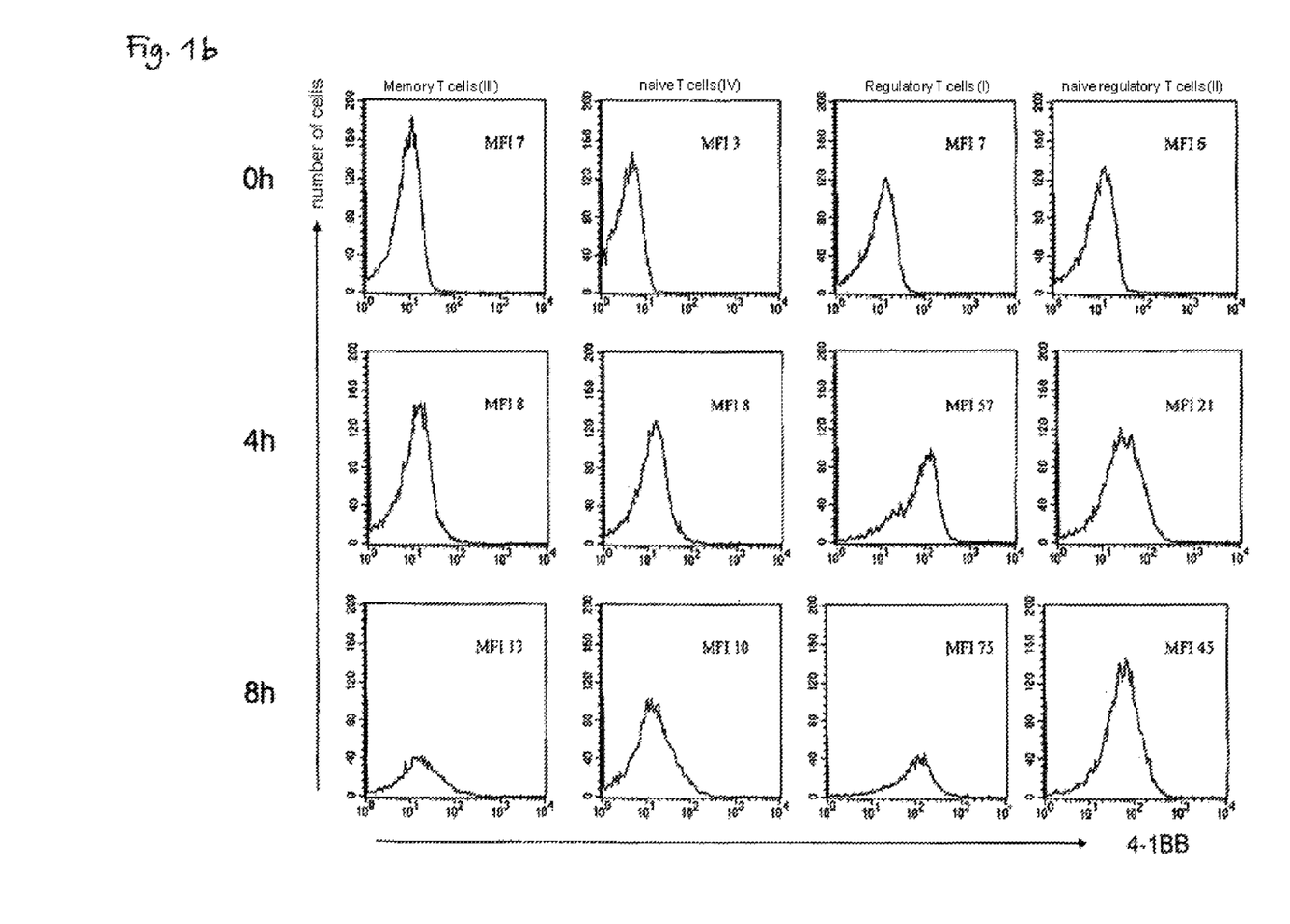
Figure 2:
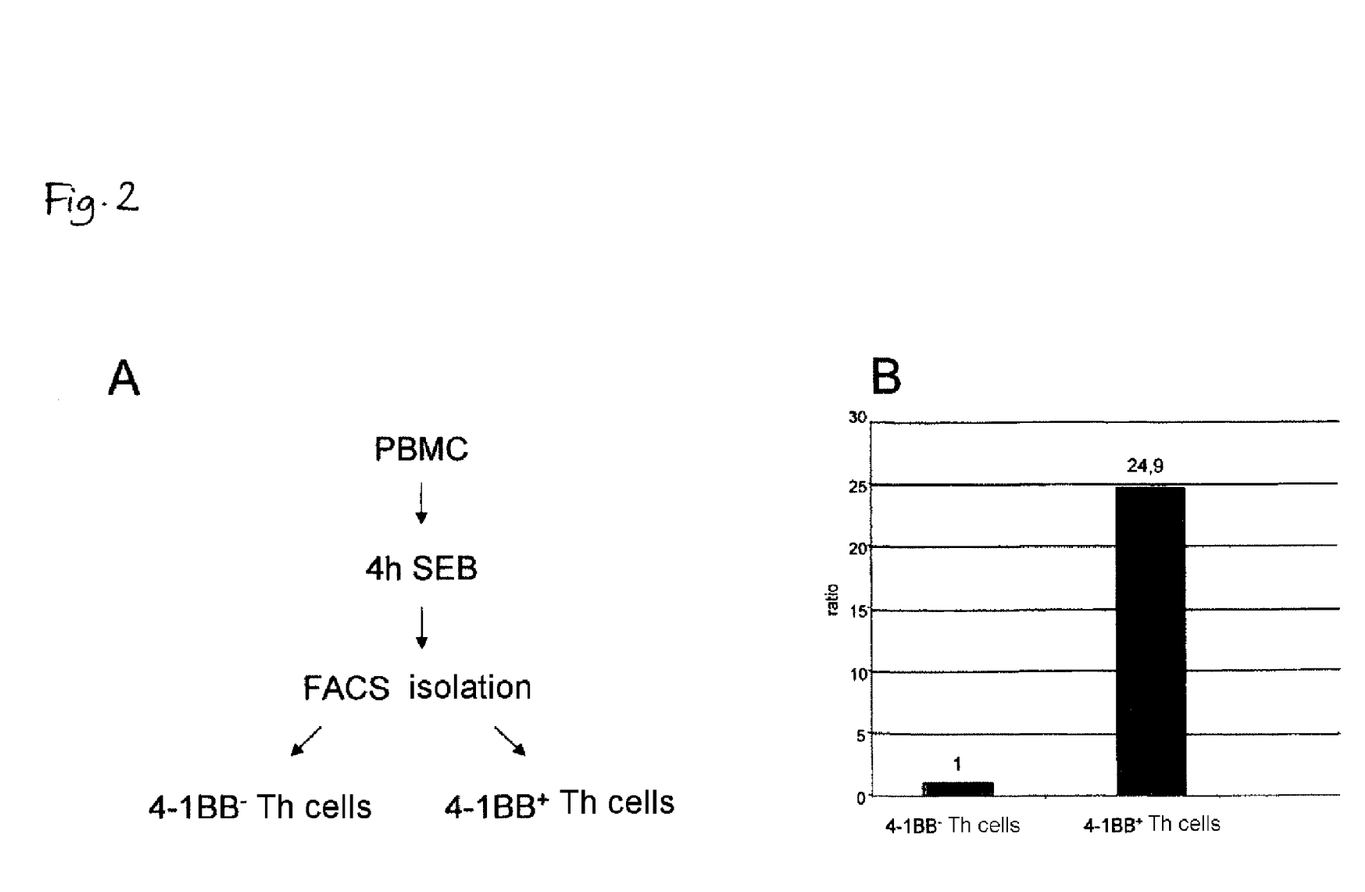
Figure 3:
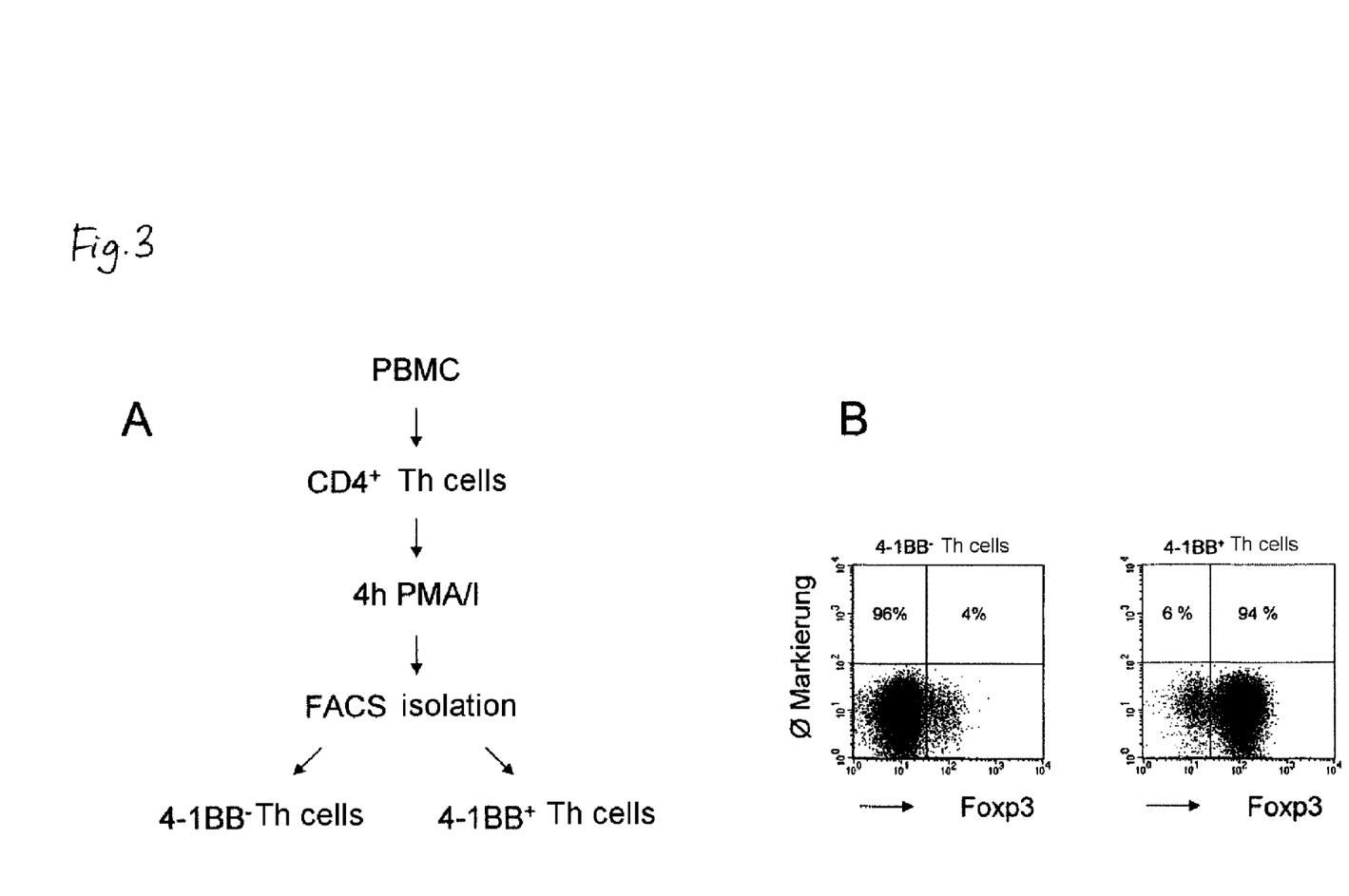
Figure 4:
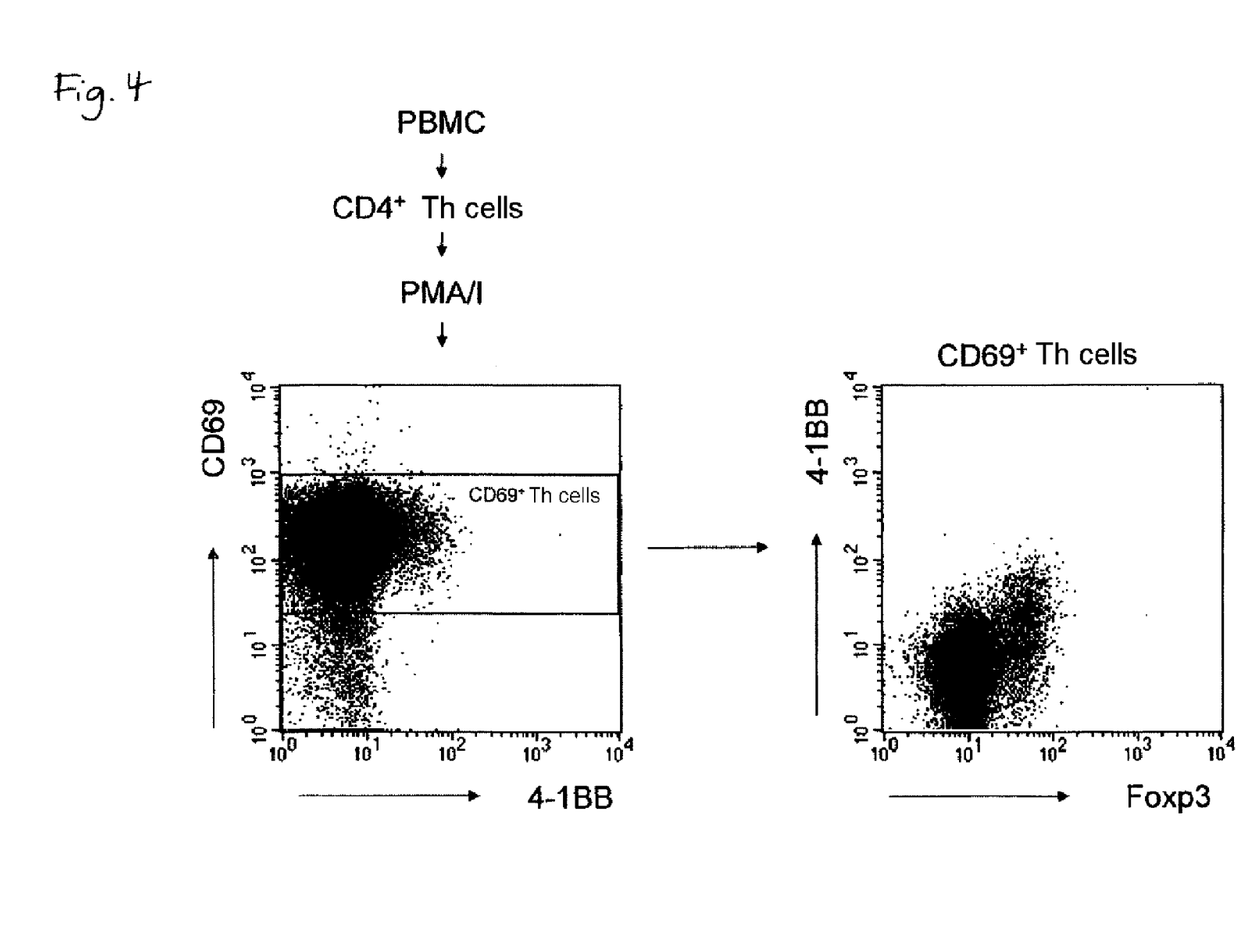
Figure 5:
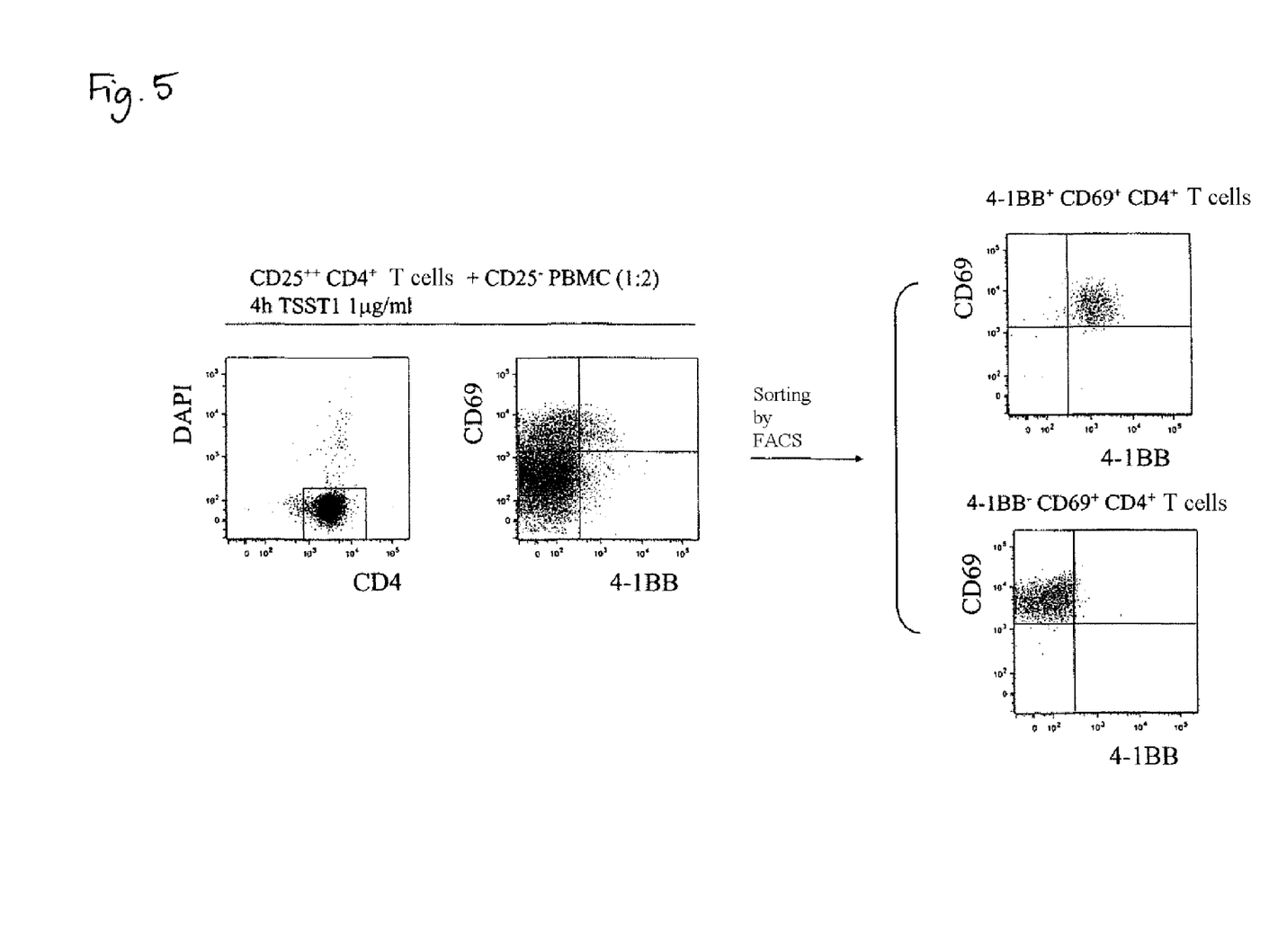
Figure 6:
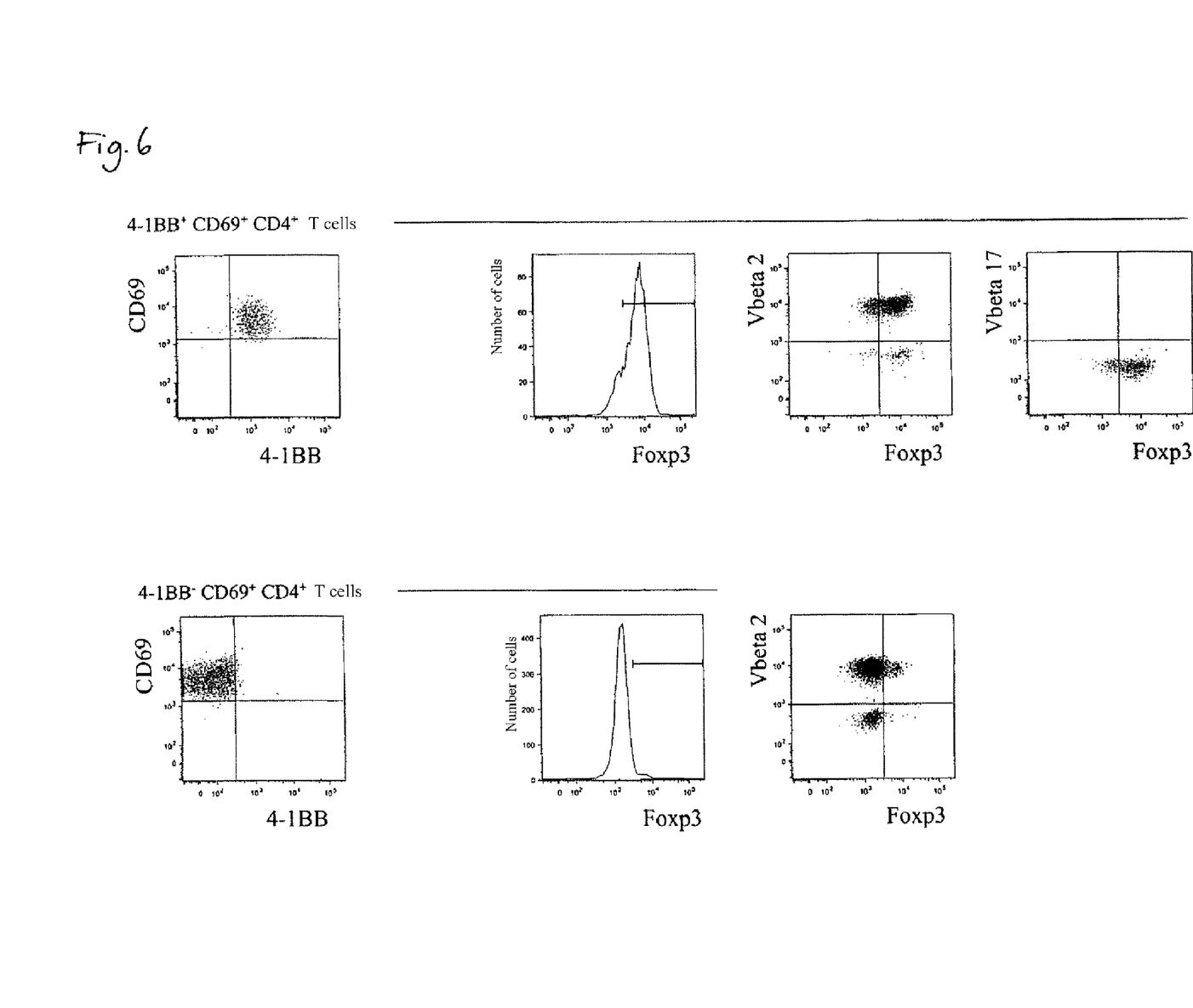
Figure 7:
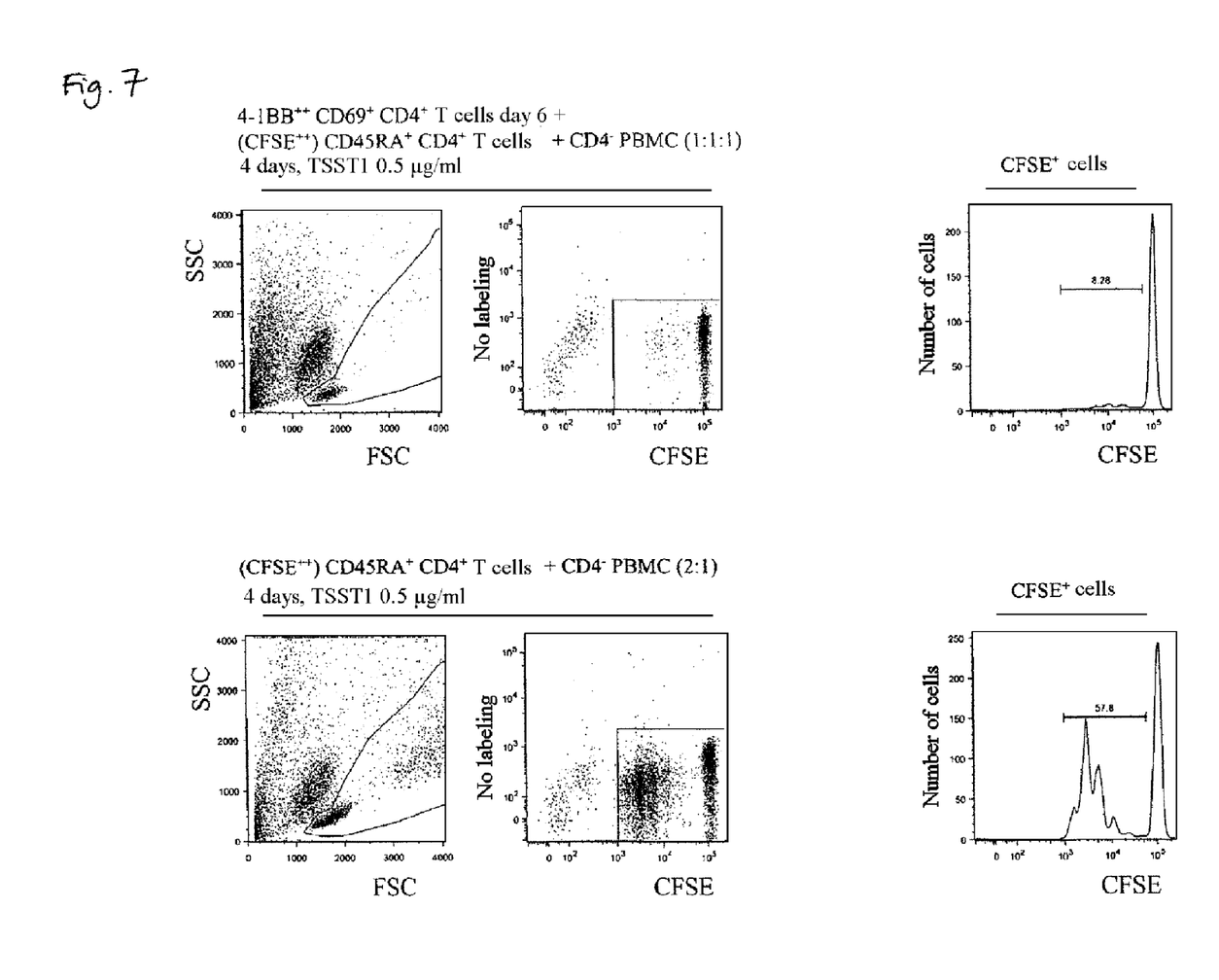

The supplemented data demonstrate firstly the specificity of the 4-1BB expression induced by stimulation with antigen (here TSST-1). In the time window of 4 hours chosen here, 4-1BB is expressed almost exclusively by Vbeta2$^+$ Foxp3$^+$ cells, while a further T-cell activation marker (CD69) described in the literature is also expressed by Foxp3$^-$ cells (FIG. 6). In addition, almost no Vbeta17$^+$ cells are detectable among the isolated 4-1BB$^+$ cells (FIG. 6). FIG. 7 then demonstrates the suppression potential of TSST-1-specific Treg after isolation and in vitro culturing. Proliferation of TSST-1-specific naïve T cells is depressed by TSST-1-specific Tregs from more than 55% to less than 10% (FIG. 7).

The invention claimed is:

1. A method for identifying and, optionally, separating activated regulatory CD4+ CD25+ Th cells comprising:
   providing a cell mixture comprising CD4+ CD25− Th cells, identifying activated regulatory CD4+ CD25+ Th cells in said mixture via a 4-1BB receptor that is expressed as a discriminating marker on said CD4+ CD25+ Th cells, and
   optionally separating said activated regulatory CD4+ CD25+ Th cells via said 4-1BB receptor.

2. The method according to claim 1, wherein the 4-1BB receptor is expressed on said activated regulatory CD4+ CD25+ Th cells asymmetrically in a time-dependent manner.

3. The method according to claim 2, wherein the time of expression of the receptor as a discriminatory marker is determined by checking for said expression repeatedly.

4. The method according to claim 2, wherein the receptor is said discriminatory marker for activated regulatory CD4+ CD25+ Th cells in a period of essentially 0 to 18 hours after an activation, preferably in a period of essentially 0 to 12 hours, particularly preferably in a period of essentially 0 to 10 hours, very particularly preferably in a period of essentially 1 to 8 hours, especially essentially 3 to 8 hours, in particular essentially 4 hours.

5. The method according to claim 1, wherein the activated regulatory CD4+ CD25+ Th cells further express FoxP3+.

6. The method according claim 1, wherein said activated regulatory CD4+ CD25+ Th cells are live regulatory Th cells.

7. The method according to claim 1, wherein said activated regulatory CD4+ CD25+ Th cells are antigen-specific regulatory Th cells.

8. The method according to claim 1, wherein the activated regulatory CD4+ CD25+ Th cells are separated by flow cytometry or magnetic cell sorting.

9. The method according to claim 1, wherein expression of the 4-1BB receptor is measured after and/or during a stimulation, wherein said stimulation activates said cells.

10. The method according to claim 1, wherein the activated regulatory CD4+ CD25+ Th cells are identified and/or separated after and/or during a stimulation of the cells in the cell mixture, wherein said stimulation activates said cells.

11. The method according to claim 1, wherein the activated regulatory CD4+ CD25+ Th cells are identified in and optionally separated from, blood, peripheral mononuclear blood cells (PBMC), body tissue or cells of tissue fluid.

12. A method according to claim 3, wherein said checking is performed regularly.

13. A method according to claim 12, wherein said checking is performed in essentially 10 to 40 minute intervals or in essentially 30 minute intervals.

14. The method of claim 9, wherein live regulatory Th cells are identified and/or separated.

15. The method of claim 1, wherein live regulatory Th cells are identified and/or separated.

* * * * *